United States Patent [19]

Seneca

[11] Patent Number: 5,219,340
[45] Date of Patent: Jun. 15, 1993

[54] COLLOIDAL OATMEAL SOLUTION APPLICATOR

[76] Inventor: Elaine Seneca, 141 Beverly Rd., Staten Island, N.Y. 10305

[21] Appl. No.: 734,476

[22] Filed: Jul. 23, 1991

[51] Int. Cl.$^5$ ................. A61M 35/00; A61F 13/00
[52] U.S. Cl. ........................ 604/290; 604/304
[58] Field of Search ............... 604/2, 289, 290, 371, 604/303, 304; 128/65; 15/104.94, 104.93, 227

[56] References Cited

U.S. PATENT DOCUMENTS

| | | | |
|---|---|---|---|
| 3,896,807 | 7/1975 | Buchalter | 604/289 |
| 3,959,841 | 6/1976 | Horne | 15/104.94 |
| 4,014,995 | 3/1977 | Juliano et al. | 424/108 |
| 4,068,666 | 1/1978 | Shiff | 604/371 |
| 4,154,542 | 5/1979 | Rasmason | 15/227 |
| 4,457,640 | 7/1984 | Anderson | 15/104.94 |
| 4,634,436 | 1/1987 | La Tour | 604/303 |
| 4,839,076 | 5/1989 | Millet et al. | 128/65 |
| 4,932,095 | 6/1990 | Kawase | 15/227 |
| 5,100,603 | 5/1992 | Rau | 424/466 |

Primary Examiner—Randall L. Green
Assistant Examiner—K. M. Reichle
Attorney, Agent, or Firm—Weingram & Zall

[57] ABSTRACT

An applicator for applying a colloidal oatmeal solution locally to one's body is provided. The applicator is formed of a porous material and contains ground oatmeal particles. The applicator includes a strap to facilitate handling and control by the user. When the applicator is immersed in water, water passes into the applicator and coacts with the oatmeal to form a colloidal oatmeal solution which may be delivered via the applicator, to any desired location on a person's body.

3 Claims, 3 Drawing Sheets

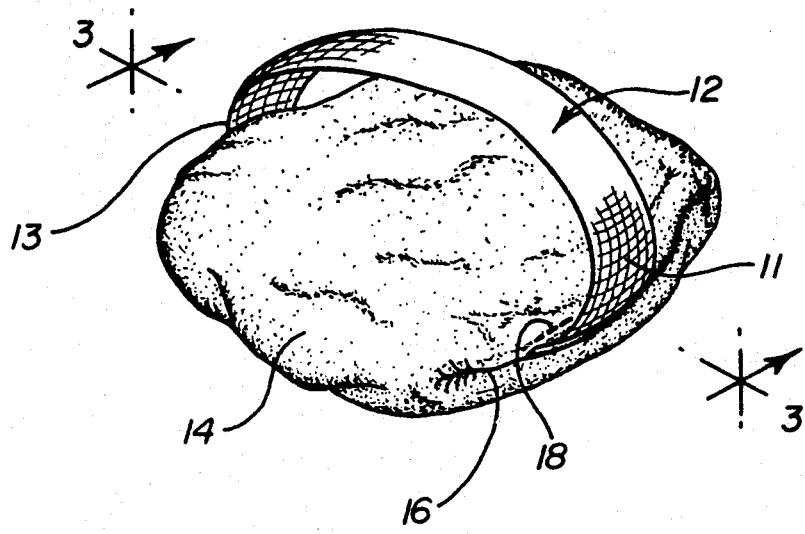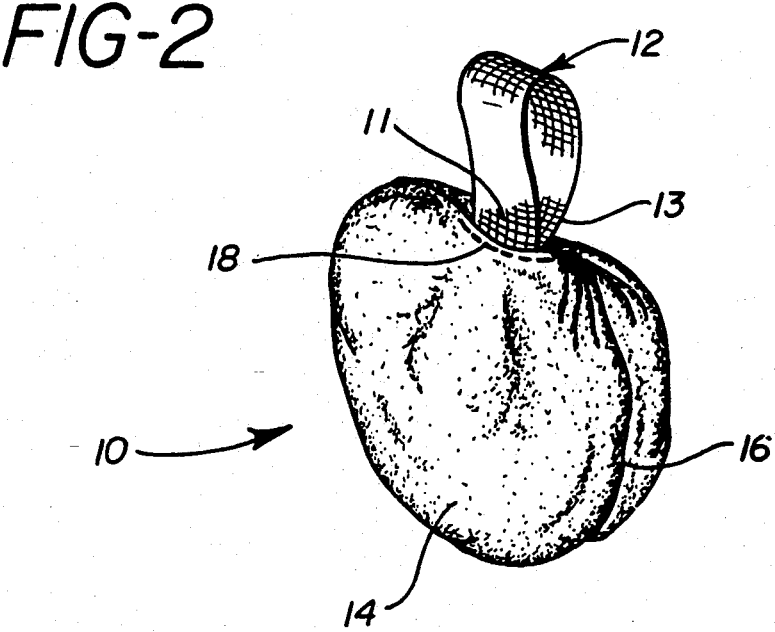

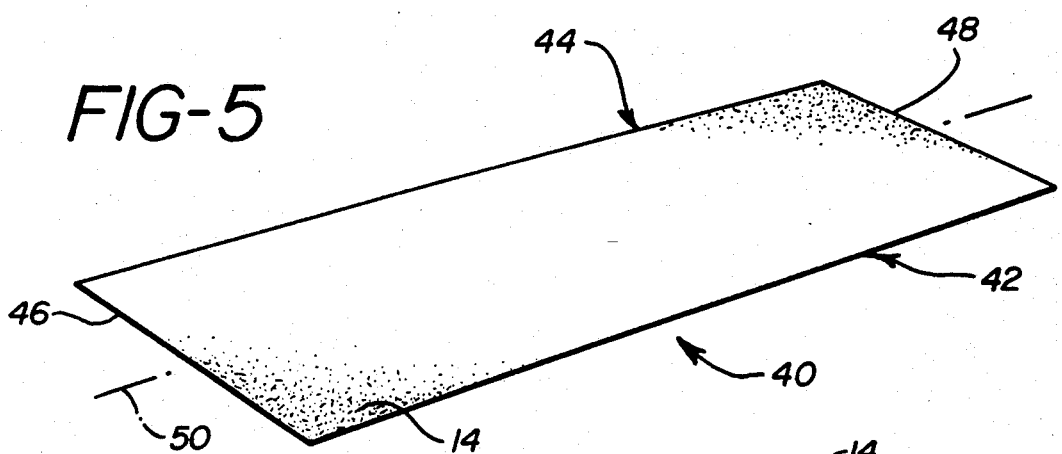
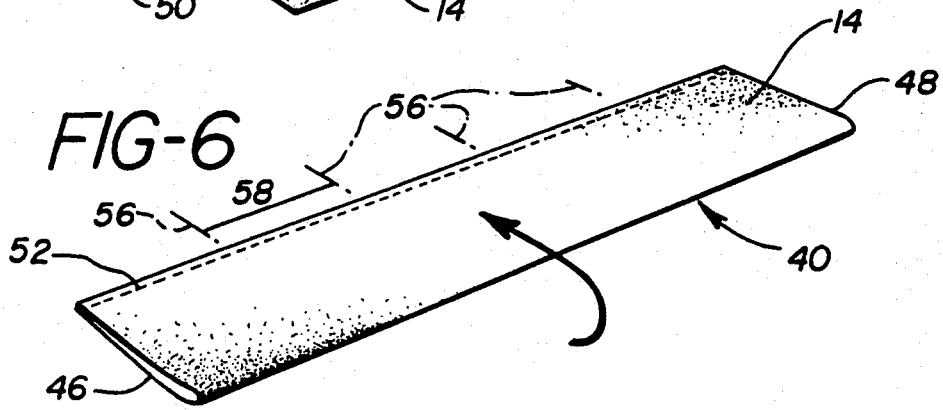
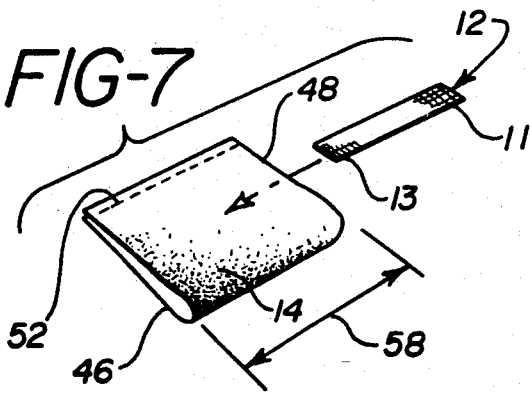
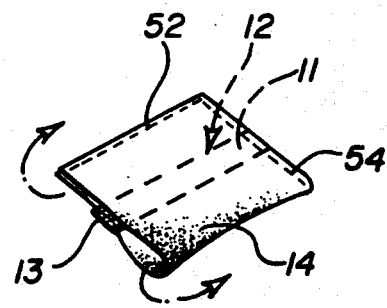
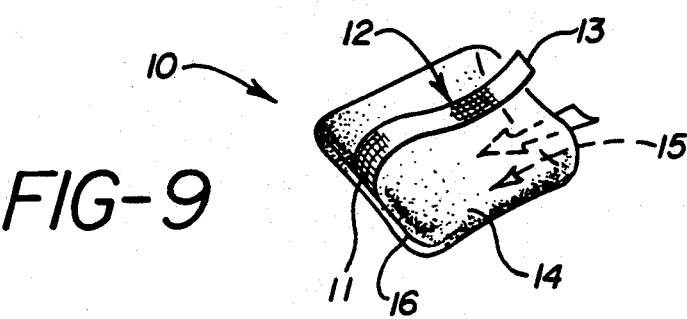

COLLOIDAL OATMEAL SOLUTION APPLICATOR

FIELD OF THE INVENTION

This invention relates to an applicator for applying a skin conditioner to a person's body, and more particularly a pouch containing oatmeal for applying a colloidal oatmeal solution to one's body.

RELATED ART

Patents have issued which relate to providing a pouch or mitt to supply a medicant or soap to a bather during either a bath or a shower. Among them is a bath or rubbing glove having a pocket in the palm thereof for retaining medicated material or rubbing compounds. Further, many soap bags have been provided, having pouches in the palms thereof for accepting soap therein, which allow for the lathering of one's body with soap. Additionally, it is well known that when applied to one's skin, oatmeal can provide a soothing, beneficial effect to the skin. However, nothing in the prior art provides the ease and convenience of use, nor the beneficial effects of the colloidal oatmeal applicator of the present invention. Further none of the patents discussed herein, either singly or in combination, teach or suggest the present invention.

Fike, U.S. Pat. No. 674,913, discloses a bath or rubbing glove, particularly for applying medicated material or rubbing compounds to the skin, having a pocket in the palm thereof for holding the material. The pocket extends lengthwise and has a protective covering secured to the glove over the pocket to retain the material therein.

Rowland et al., U.S. Pat. No. 736,786, discloses a powder-puff particularly for use in applying talcum powder to the body, having a pocket in which the fingers and palm can be inserted so that the powder-puff can be readily manipulated to successfully reach any portion of the body.

Hagerling, U.S. Pat. No. 2,089,057, discloses a waxing pad, particularly for use in waxing automobiles, furniture and other articles where a waxed surface is desired, having a front part of soft porous material, which, together with a back pad, forms a hollow compartment adapted to hold a quantity of wax. The waxing pad has an opening in its side for allowing replenishment of the wax and also has a drawstring adapted to close the compartment to prevent wax from exiting therethrough.

Topjian, U.S. Pat. No. 2,233,686, discloses a powder puff in the form of a mitt having a powder applying surface. The puff is of a durable structure. The puff also has the capacity for holding a large supply of powder. Further, the powder can escape only through the powder applying surface thereby insuring the application of powder to the desired areas and minimizing waste of powder.

Halley, U.S. Pat. No. 2,501,565, discloses mittens for applying skin cream to one's hands. The mittens are especially adapted to be worn during treatment of the hands and prevent the cream from rubbing off on clothing or bedding. Each mitten includes an inner mitt which is impervious to grease, and which is impregnated with a skin cream so that the hands are treated with the cream merely by wearing the mitten. The inner mitts are readily removable from the outer mitts to facilitate replacement.

Miller, U.S. Pat. No. 2,607,940, discloses a soap bag, of an open mesh material having a pocket for receiving the fingertips of the user so that it will not easily slip out of the grasp of the user.

Green, U.S. Pat. No. 3,081,480, discloses a disposable applicator which contains its own supply of polish for polishing a shoe. The applicator has a pervious portion and an impervious portion. The applicator is grasped on the impervious portion between one's thumb and the fingers, and the pervious portion of the applicator, through which the polish may pass is applied to the surface of a shoe without soiling the user'hand.

Billesbach et al., U.S. Pat. No. 3,777,121, discloses a soap pouch assembly particularly for lathering one's body with soap, having a pouch with an open side and a closure flap adapted to be folded over the open side to close the pouch.

Baker, U.S. Pat. No. 3,776,644, discloses a packet, particularly used to package messy spreadable compositions such as polishes and lotions. The packet is also convertible to a applicator. The packet is made of a flexible sheet material which includes a fusible thermoplastic layer and a nonfusable backing layer having a nonfibrous rear surface. The sheet material forming each opposing wall extends beyond a seal formed along one edge of the envelope cavity to form a pair of outwardly projecting ear flaps. The ear flaps are adapted to be gripped between a thumb and forefinger and drawn apart to rupture the seal to convert the packet into an applicator.

Rasmason, U.S. Pat. No. 4,154,542, discloses a shower mitt for applying soap to one's body during a shower, having a retaining mesh nylon net enclosure applied to the palm portion of the mitt. A zippered opening is provided in the interior of the mitt to permit access to the enclosure so that it may be opened for placement of soap into the enclosure.

Anderson, U.S. Pat. No. 4,457,640, discloses a body wash pad for bathing, having a sponge core and a terry cloth covering. The terry cloth covering forms a pocket equipped with a closure which provides a container for soap.

The related art does not provide the essential elements of the present invention, nor does it disclose the beneficial effects of the present invention.

SUMMARY OF THE INVENTION

The present invention sets forth an applicator for applying a colloidal oatmeal solution to the skin of a person. Typically, the applicator is in the form of a pouch of a porous material having ground oatmeal contained therein. In use, the applicator is immersed in warm water, the water passing into the pouch and coacting with the oatmeal to create a colloidal oatmeal solution. The applicator is then removed from the water and brought into contact with one's skin where the colloidal oatmeal solution passes through and exits the pouch onto a person's skin. In this way, this invention permits the colloidal oatmeal solution to be delivered locally to one's body for soothing and conditioning one's skin in specific locations. The porous material is sufficiently porous for water to pass therethrough but not so great as to allow particles of ground oatmeal to do so.

Also included in the present invention is a method of manufacturing and assembling the colloidal oatmeal applicators of the present invention comprising folding a length of the porous material along its longitudinal axis, to align the top and bottom edges, fastening of the top and bottom edges together, shearing the length of material into sections, fastening together one of the open edges of a section, turning the section inside-out to hide the seams, loading ground oatmeal into the section through the remaining open edge thereof, and fastening the remaining open edge together to seal the oatmeal within the pouch. Additionally, a strap may be incorporated into the pouch, during the manufacture thereof, to facilitate ease of control of the pouch by a user.

Accordingly, it is an object of the present invention to provide an apparatus for applying a colloidal oatmeal solution to the body which can be easily and conveniently used.

It is another object of the present invention to provide an apparatus for applying a colloidal oatmeal solution locally to one's body.

It is also an object of the present invention to provide an apparatus for applying a colloidal oatmeal solution to the skin of a user for use in showering, or during basin-type washing, or during a bath.

It is still another object of the present invention to provide an apparatus for applying a colloidal oatmeal solution to the body of one who is unable to bath or shower in a conventional manner.

A further object of the present invention is to provide an apparatus for applying a colloidal oatmeal solution to one's body which is relatively inexpensive to manufacture and easily disposable.

These, as well as further objects and advantages of this invention, will become apparent to those skilled in the art from a review of the accompanying Detailed Description of the Preferred Embodiment, reference being made to the accompanying drawings.

BRIEF DESCRIPTION OF THE DRAWINGS

FIG. 1 is a perspective view of the colloidal oatmeal applicator of the present invention.

FIG. 2 is a perspective view of an alternative embodiment of the colloidal oatmeal applicator of the present invention, showing the strap in one of its many alternate positions;

FIG. 5 is perspective view of a length of the porous material of the applicator of the present invention.

FIG. 6 is a perspective view of the length of porous material of FIG. 5 folded along its longitudinal axis;

FIG. 7 is a perspective view of a section of the length of porous material of FIG. 6 showing the insertion of a strap therein;

FIG. 8 is a perspective view of the section of porous material of FIG. 7 showing the fastening of one free edge together; and FIG. 9 is a perspective view showing the manner in which oatmeal is placed within the pouch.

DETAILED DESCRIPTION OF THE PREFERRED EMBODIMENTS

Figure 3:
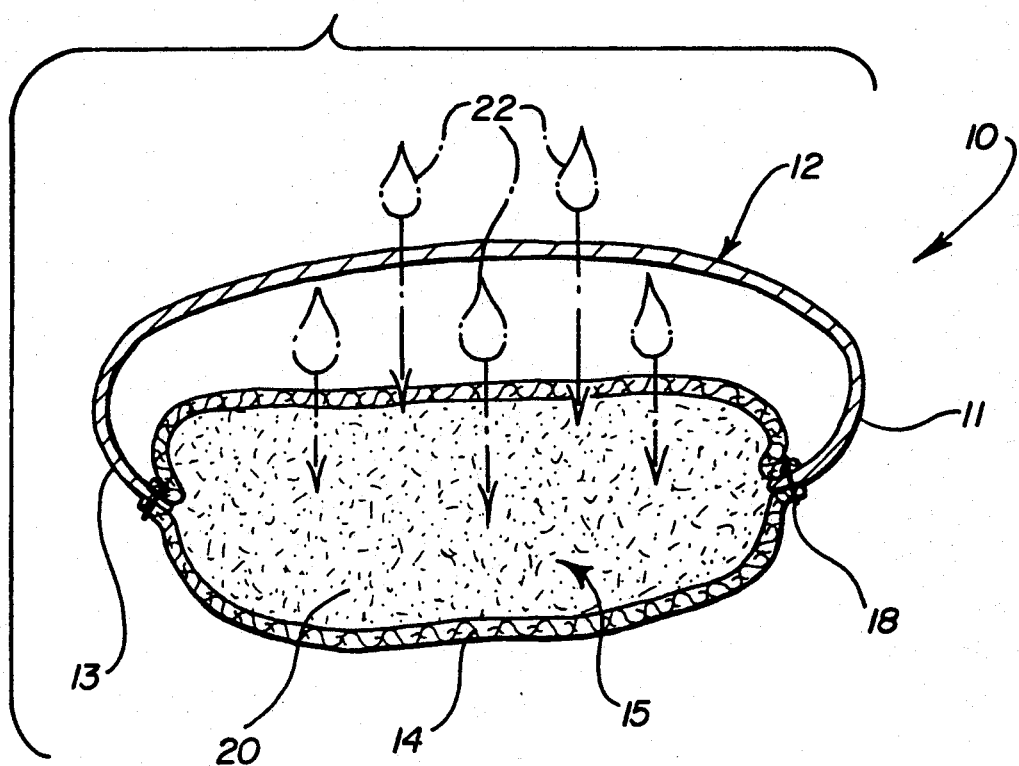
FIG. 3 is a cross-sectional view taken along line 3—3 of the applicator of FIG. 1 showing, in broken lines, the penetration of water into the applicator.

Referring to FIG. 1, the colloidal oatmeal solution applicator, generally indicated at 10, is shown. The applicator 10 is formed of a porous material 14. The porous material is formed in the shape of a pouch, typically by means of sewing two pieces of the porous material 14 together or by folding one length of porous material 14 upon itself, and sewing the edges together to create a seam 16. Within the pouch, oatmeal is contained. The use of the term "oatmeal" is meant to include not only oatmeal as is commonly known, but may include other seeds from cereal, grass, and grains, e.g. wheat, corn, rye, rice, and millet. Typically, the oatmeal used is 100% ground rolled oats, though beneficial results may be achieved by combining the oats with 50% oat flour. Preferably, but not necessarily, included as part of the applicator 10 is hand strap 12 which facilitates positioning the applicator 10 by the user to the desired location of one's body. Strap 12 is, in this embodiment of the applicator, attached across the pouch and fastened at the seams of opposite edges with stitches 18.

Referring to FIG. 2, another embodiment of the applicator 10 is shown. In this embodiment, the applicator 10 is sewn such that a rounded pouch is formed. The applicator 10 includes a strap, both ends, 11 and 13, of which are anchored to the same position of the applicator with anchor stitches 18. Thus, in this embodiment, strap 12 forms a loop through which a finger may be passed. Again, the strap facilitates handling and positioning of the applicator 10 to deliver a colloidal oatmeal solution to a desired location of one's body. By the use of the term "colloidal oatmeal solution" it is meant the aqueous composition produced by the contacting of water with the oatmeal grains contained within the pouch, which composition passes through the pores of the porous material forming the pouch. This composition may range from a true solution to an aqueous solution of water soluble components contained in the oatmeal.

Figure 4:
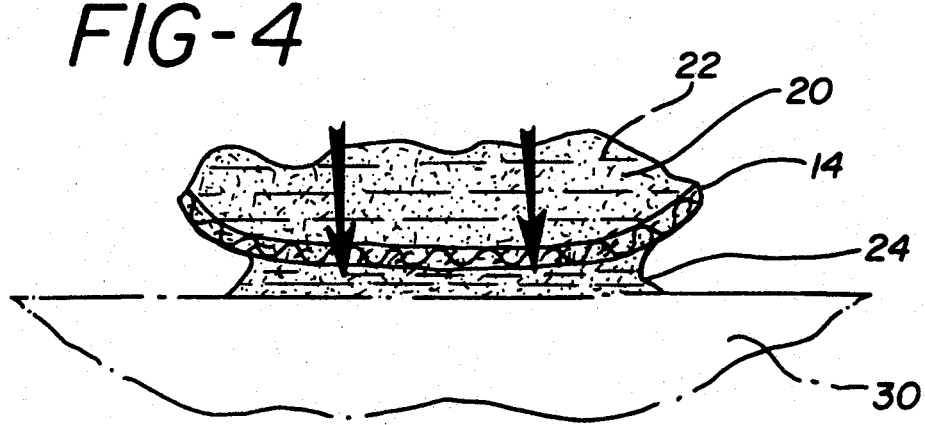
FIG. 4 is an enlarged fragmentary cross-sectional view of the applicator of FIG. 3 showing the release of the colloidal oatmeal solution from the applicator.

Referring to FIGS. 3 and 4, the operation of the applicator 10 is depicted. As indicated in FIG. 3, when the applicator 10 is brought into contact with water 22, typically by immersing the applicator 10 into a volume of water, the water passes through the porous membrane 14 and enters the inside cavity 15 of applicator 10. Upon entry into the inside cavity 15, the water coacts with the ground oatmeal to form a colloidal oatmeal solution 24. The porous material 14 is of a sufficient porosity to allow for water and for the colloidal oatmeal solution 24 pass therethrough, but not so porous so as to allow the ground oatmeal particles 20 to pass therethrough.

As may be seen in FIG. 4, after the applicator 10 is removed from the water bath, and the water has had sufficient time to coact with the ground oatmeal particles 20 to form a colloidal oatmeal solution 24, the applicator may be placed into contact with a person's skin 30. Gentle pressure applied to the applicator 10 along with movement of the applicator 10 along the person's skin 30 results in the application of the colloidal oatmeal solution 24 through the porous membrane 14 to the persons skin 30. The applicator 10 allows one to apply a colloidal oatmeal solution locally to desired locations of one's body. Further, the applicator 10 permits the application of a colloidal oatmeal solution to the skin of one who is unable to immerse their entire body into a colloidal oatmeal bath but still necessitates or desires application of a colloidal oatmeal solution to various locations on their body that can only be reached by means of the applicator 10 of the present invention.

The applicator 10 of the present invention has numerous beneficial aspects. First, it can be used in a wide variety of settings, i.e., in a bathtub, in a shower, during pan washing an in connection with a wash basin. Further, the applicator may be placed directly into a water bath and allowed to release the colloidal oatmeal solution directly into the bath water. Additionally, the applicator may be grasped directly or may be grasped indirectly by means of the strap. The use of the applicator is relatively simple, i.e., the pouch must be placed into a bath and then applied to one's skin. No adjustments are necessary for use by any individual. The porous material is non-abrasive and is therefore unlikely to scratch or irritate one's skin. The porous material is also quite flexible and may be deformed to any desired shape. Finally, the applicator, upon reaching the end of its useful life, may be easily disposed. The colloidal oatmeal applicator has been shown to relieve rashes by soothing inflamed skin, enhancing beauty by bringing out the natural lustre of skin, conditioning the skin, fighting acne, and restoring proper pH balance to skin.

Referring to FIGS. 5-9, the steps of a method of manufacturing the applicator are shown. FIG. 5 shows a length of porous material, generally indicated at 40, having a bottom edge 42, a top edge 44 a lower edge 46, an upper edge 48 and a longitudinal axis 50 extending along the length of the porous material 40.

As can be seen in FIG. 6, the first step of the method of manufacturing the colloidal oatmeal solution applicator 10 of the present invention comprises folding the length of porous material 40 along its longitudinal axis 5 so that the bottom edge 42 is placed along the top edge 44. Then, the top edge and bottom edge are fastened together, typically being sewn by stitches 52. Next, the length of porous material 40 is cut into applicator lengths. The cutting takes place along the width of the length of porous material at applicator lengths 56 (indicated by hash marks).

Referring to FIG. 7 after the applicator lengths 56 are cut from the length of porous material 40, a strap 12 is placed within the fold. The strap 12 is positioned parallel to the fold of the porous material and between the fastened edges of the porous material and the fold. Next, as shown in FIG. 8, one of the open edges of the porous material is fastened, typically by means of a stitch 54. Typically, the stitch 54 also passes through end 11 of strap 12 to anchor the strap 12 to the applicator 10. Then, as indicated by the arrows of FIG. 8, the porous material is turned inside-out to position the seams 52 and 54 of the two edges of the porous material within the cavity 15 formed of porous material.

Finally, as shown in FIG. 9, the cavity 15 of the porous material 14 may be filled with ground oatmeal particles 20, as indicated by the arrow, the remaining open side of the applicator sewn closed, and the free end 13 of strap 12 anchored to the applicator.

For forming the first embodiment of the applicator of the present invention, the length of material is cut to a width of 7 inches, so that when folded over, the resulting width of the applicator is 3½ inches. Then, the applicator lengths are cut in 4 inch increments. Thus, an applicator having the dimensions of 3½ by 4 inches is created. For forming the second embodiment of the applicator, preferably, though not necessarily, the length of porous material is cut 6 inches in widths, so that when it is folded over, the resulting width of the applicator is 3 inches. Then, the applicator lengths are cut at 3 inch increments to form an applicator having the dimensions of 3 inches by 3 inches.

For best results the strap is 5½ inches long, though, straps of any dimension are within the scope of the invention. Preferably, the seems are formed approximately ⅛ of an inch from the edges of the porous material, though again, positioning of seams in any other location is included within the scope of this invention. The ends may be sewn with a few number of stitches, e.g., 8 stitches, to give a tucked look to the bag.

Preferably the cavity of the applicator should be filled with 2 ounces of ground oatmeal particles, though more or less, is still within the scope of the invention.

In the preferred embodiment of this invention, the porous material is 100% batiste cotton, though other cotton blends, such as 50% cotton and 50% polyester or 65% polyester and 35% cotton also perform satisfactorily, and along with any other suitable porous material, are considered within the scope of this invention.

Having thus described my invention in detail, it is to be understood that the foregoing description is not intended to limit the scope thereof. What is desired to be protected by Letters Patent is set forth in the appended claims.

What is claimed:

1. A method of manufacturing an applicator for applying an oatmeal treatment to a person's skin comprising:
   providing a length of porous material having a length, a width, a longitudinal axis extending the length of the porous material, a top edge, and a bottom edge, the material having sufficient porosity to permit a colloidal oatmeal solution to pass therethrough yet substantially preventing dry oatmeal particles from passing therethrough;
   folding the porous material in half along the longitudinal axis to place the top edge and the bottom edge in overlying relationship;
   fastening the top edge to the bottom edge;
   cutting the length of material, along the width thereof, into applicator lengths;
   positioning a strap within the applicator length parallel to the fold and between the fold and the fastened edges;
   fastening together one of the open edges of the applicator length, and anchoring one end of the strap therebetween;
   turning the applicator length inside out to conceal within the applicator the fastened edges;
   filling the applicator, through the remaining open edge thereof, with dry oatmeal particles which, when contacted with water, forms a colloidal oatmeal solution that can pass through the porous material; and
   fastening together the remaining open edge of the applicator and anchoring the free end of the strap therebetween.

2. The method of claim 1, wherein the step of fastening the edges together is accomplished by sewing the edges together.

3. The method of claim 1, wherein the prior to being placed into the applicator, oatmeal is ground into the dry oatmeal particles.

* * * * *